(12) United States Patent
Cho et al.

(10) Patent No.: US 6,440,760 B1
(45) Date of Patent: Aug. 27, 2002

(54) METHOD OF MEASURING ETCHED STATE OF SEMICONDUCTOR WAFER USING OPTICAL IMPEDENCE MEASUREMENT

(75) Inventors: Hyung-suk Cho; Sang-mun Chon; Sang-bong Choi; Chung-sam Chun; Min-sub Kang, all of Kyungki-do (KR)

(73) Assignee: Samsung Electronics Co., Ltd. (KR)

( * ) Notice: Subject to any disclaimer, the term of this patent is extended or adjusted under 35 U.S.C. 154(b) by 0 days.

(21) Appl. No.: 09/663,644

(22) Filed: Sep. 18, 2000

(30) Foreign Application Priority Data

Sep. 18, 1999 (KR) ............................................. 99-40289
Jul. 21, 2000 (KR) ........................................ 2000-41921

(51) Int. Cl.[7] ............................................. G01R 31/26
(52) U.S. Cl. ...................... 438/16; 365/355; 250/492.2
(58) Field of Search ................................ 438/637, 108; 257/737; 250/442.2; 356/355

(56) References Cited

U.S. PATENT DOCUMENTS 5,055,696 A * 10/1991 Haraichi .................. 250/492.2
5,982,489 A * 11/1999 Shiraishi ...................... 356/355

* cited by examiner

*Primary Examiner*—John F. Niebling
*Assistant Examiner*—Andre C Stevenson
(74) *Attorney, Agent, or Firm*—Myers Bigel Sibley & Sajovec

(57) ABSTRACT

Embodiments of the present invention include methods for measuring a semiconductor wafer which has been subjected to an etching process. Light is radiated at the semiconductor wafer. Light within a selected wavelength band reflected from the semiconductor wafer is measured to provide an output value. A ratio of the output value and a reference value is determined. The reference value may be based on light within the selected wavelength band reflected from a reference surface, such as a bare silicon reference surface. It is determined that the semiconductor wafer is under-etched if the determined ratio does not meet the reference value. A normalized optical impedance or a polarization ratio may be measured based on light within a selected wave length band reflected from the semiconductor wafer to provide the output value in various embodiments of the present invention. In further aspects of the present invention, a thickness of a remaining oxide layer is determined using an under-etch recipe when it is determined that a semiconductor wafer is under-etched and a thickness of a damaged/polymer layer may be determined using an over-etch recipe when it is determined that the semiconductor wafer is over-etched.

67 Claims, 8 Drawing Sheets

METHOD OF MEASURING ETCHED STATE OF SEMICONDUCTOR WAFER USING OPTICAL IMPEDENCE MEASUREMENT

RELATED APPLICATIONS

This application is related to Korean Application No. 99-40289, filed Sep. 18, 1999 and Korean Application No. 00-41921, filed Jul. 21, 2000, the disclosures of which are hereby incorporated herein by reference.

FIELD OF THE INVENTION

The present invention relates methods for measuring semiconductor wafers, for example, during the manufacture of a semiconductor device, and more particularly, methods for measuring semiconductor wafers which have undergone an over-etching process.

BACKGROUND OF THE INVENTION

When manufacturing semiconductor devices, a dry etching type of contact etching process using over-etching may be applied to form, for example, a direct contact (DC) or a buried contact (BC). Such process may sufficiently etch oxide taking into account the uniformity of the etching process itself. A single crystalline silicon substrate (a wafer) may be over-etched during an etching process, but poly crystalline silicon, not the silicon substrate, is typically over-etched during an etching process for forming a BC, and metal is typically over-etched during a process of forming a metal contact (MC).

After an over-etching process has been performed, the completion of the over-etching process is generally determined based on presence/absence of oxide remaining at an oxide site and the measured thickness of the remaining oxide. Typically, when the film structure of an oxide site is inspected after an over-etching process, it can be seen that oxide is over-etched down to a silicon substrate. Accordingly, the success or failure of over-etching generally can be determined by measuring the thickness of the remaining oxide at an oxide site that has undergone an over-etching process.

However, most conventional measuring equipment has been considered unsuitable for monitoring an over-etching process because an under-etched state of a film typically cannot be exactly discriminated from an over-etched state of a film based on a value measured by the measuring equipment.

FIG. 1 is a graph showing the results of measuring the thickness of remaining oxide (Tox) using an optical measuring apparatus with respect to wafers which are obtained after dry-etching active silicon nitride (SiN) during manufacture of 64-M dynamic random access memory (DRAM) devices. In the process of accumulating measurement data, one wafer is sampled on each day. For example, as shown in FIG. 1, the measured values of the thickness of remaining oxide at an oxide site which has undergone dry etching of SiN are uniformly maintained in a range of 0–5 Å (angstroms). Based on the fact that the measured values occupy a very small range, an operator can generally determine whether or not an over-etching process is performed normally and successfully.

FIG. 2 is a graph showing the results of measuring the thickness of remaining oxide with respect to wafers which are obtained after over-etching the oxide for forming a DC during manufacture of 64-M DRAM devices. In the process of accumulating measurement data, five wafers are sampled on each day. FIG. 2 shows the measured results with respect to wafers on which over-etching has been completed based on actual measurement.

As shown in FIG. 2, despite the actual successful over-etching of a wafer during an oxide etching process for forming a DC, the measured results do not always allow an operator to determine that the over-etching is successfully completed. As shown in FIG. 2, the measured values of the thickness of remaining oxide on a wafer on which over-etching is actually completed are distributed throughout a range of 0–100 Å. Accordingly, when a measured value is about 90 Å, that is, when it is determined that oxide of a thickness of about 90 Å remains, it is difficult to determine the success or failure of over-etching based on this value.

As the measured results of conventional measuring equipment may be inaccurate, conventionally, the thickness of remaining oxide detected when over-etching is successfully achieved, is set to within a very wide range of 0–400 Å in the case of an over-etching process for forming a DC, and to within an even wider range of 0–1000 Å in the case of an over-etching process for forming a MC. Accordingly, oxide that is not actually etched within this range may not be monitored, thereby potentially causing process failures.

SUMMARY OF THE INVENTION

Embodiments of the present invention include methods for measuring a semiconductor wafer which has been subjected to an etching process. Light is radiated at the semiconductor wafer. Light within a selected wavelength band reflected from the semiconductor wafer is measured to provide an output value. A ratio of the output value and a reference value is determined. The reference value may be based on light within the selected wavelength band reflected from a reference surface, such as a bare silicon reference surface. It is determined that the semiconductor wafer is under-etched if the determined ratio does not meet the reference value. A normalized optical impedance or a polarization ratio may be measured based on light within a selected wave length band reflected from the semiconductor wafer to provide the output value in various embodiments of the present invention. In further aspects of the present invention, a thickness of a remaining oxide layer is determined using an under-etch recipe when it is determined that a semiconductor wafer is under-etched and a thickness of a damaged/polymer layer may be determined using an over-etch recipe when it is determined that the semiconductor wafer is over-etched.

In further embodiments, the present invention provides methods of determining the etched state of a semiconductor wafer. The methods include the steps of radiating light at bare silicon and obtaining a reference value from an electrical signal generated by light within a predetermined wavelength band of the light reflected from the bare silicon, radiating light within the predetermined wavelength band at a target of measurement, i.e., a wafer that has undergone an over-etching process, obtaining an output value corresponding to the reference value from an electrical signal generated by light within the predetermined wavelength band of the light reflected from the wafer, calculating the ratio of the output value to the reference value, and comparing the calculated ratio with a predetermined reference ratio to determine whether or not the wafer is under-etched.

In other embodiments, the present invention provides methods of determining the etched state of a semiconductor wafer. The methods include the steps of radiating light at bare silicon and obtaining a reference value by integrating an electrical signal generated by light within a predetermined wavelength band which is reflected from the bare silicon, radiating light within the predetermined wavelength band at a target of measurement, i.e., a wafer that has undergone an over-etching process, obtaining an output value by integrating an electrical signal of the predetermined wavelength band of light reflected from the wafer, calculating a ratio of the output value to the reference value, and comparing the calculated ratio with a predetermined reference ratio to determine whether or not the wafer is under-etched.

In yet further embodiments, the present invention provides methods of measuring the etched state of a semiconductor wafer. The methods include a first step of radiating light within a predetermined wavelength band at a wafer that has undergone a plasma over-etching process, a second step of obtaining a predetermined output value from an electrical signal corresponding to light reflected from the wafer, a third step of determining whether an optical impedance of the light reflected from the wafer changes based on the output value, a fourth step of determining whether the over-etching process is successfully completed depending on the change in the optical impedance determined in the third step, a fifth step of measuring the thickness of a wafer film according to a recipe employing a predetermined over-etching completed film stack when it is determined that the over-etching process is successfully completed, and a sixth step of measuring the thickness of a wafer film according to a recipe employing a predetermined over-etching incompleted film stack when it is determined that the over-etching process is not successfully completed.

In still other embodiments, the present invention provides methods of measuring the etched state of a semiconductor wafer. The methods include a first step of radiating light at bare silicon and obtaining a reference value 1 from an electrical signal generated by light within a predetermined wavelength band among the light reflected from the bare silicon, a second step of radiating light within the predetermined wavelength band at a target of measurement, i.e., a wafer that has undergone an over-etching process, a third step of obtaining an output value 1 corresponding to the reference value 1 from an electrical signal of light within the predetermined wavelength band among the light reflected from the wafer, a fourth step of calculating a ratio of the output value 1 to the reference value 1, a fifth step of comparing the calculated ratio with a predetermined reference ratio to determine whether or not the wafer is under-etched, a sixth step of measuring the thickness of remaining oxide using a predetermined under-etch recipe when it is determined that the wafer is under-etched, a seventh step of obtaining a predetermined output value 2 from an electrical signal corresponding to light reflected from the wafer when it is determined that the wafer is not under-etched, an eighth step of determining whether an optical impedance to the light reflected from the wafer changes based on the output value 2, a ninth step of determining whether or not the over-etching process is successfully completed depending on the change in the optical impedance determined in the above step, a tenth step of measuring the thickness of a wafer film according to a recipe employing a predetermined over-etching completed film stack when it is determined that the over-etching process is successfully completed, and an eleventh step of measuring the thickness of a wafer film according to a recipe employing a predetermined over-etching incompleted film stack when it is determined that the over-etching process is not successfully completed.

In yet further embodiments, the present invention provides methods of measuring the etched state of a semiconductor wafer. The methods include a first step of radiating light within a predetermined wavelength band at a wafer that has undergone a plasma over-etching process, a second step of obtaining predetermined optical impedances 1 and 2 from an electrical signal corresponding to light reflected from the wafer, a third step of comparing the optical impedance 1 with a predetermined reference impedance 1 to determine whether or not the wafer is completely over-etched, a fourth step of measuring the thickness of a wafer film according to a recipe employing a predetermined over-etching completed film stack when it is determined that the over-etching process is successfully completed in the third step, a fifth step of comparing the optical impedance 1 with a predetermined reference impedance 1 to determine whether or not the wafer is completely over-etched when it is determined that the over-etching process is not completed in the third step, a sixth step of measuring the thickness of a wafer film according to a recipe employing a predetermined over-etching completed film stack when it is determined that the over-etching process is successfully completed in the fifth step, and a seventh step of measuring the thickness of a wafer film according to a recipe employing a predetermined over-etching incompleted film stack when it is determined that the over-etching process is not successfully completed.

The reference ratio may be 92%, and the wavelength band may be 190–826 nm. The reference value is obtained from a normalized output value corresponding to an electrical output signal generated by light within the above wavelength band of the light reflected from the bare silicon, and the output value may be obtained from a normalized output value corresponding to an electrical output signal generated by light within the wavelength band of the light reflected from the wafer.

The over-etching incompleted film stack may be set to [oxide/silicon], and the over-etching completed film stack may be set to [polymer/oxide/damaged layer/silicon]. The thickness of the oxide may be set to 0. In the measuring step using the film stack, the thickness of the oxide need not be measured, but the thickness of the damaged layer and the polymer may be measured, because the oxide and the polymer typically have similar optical properties, and because if over-etched the oxide does not remain, but the polymer may be present. A damaged layer may indicate a damaged silicon layer formed on the surface of the wafer by plasma during the etching process.

The thickness of the oxide remaining on the silicon may be calculated from the electrical signal according to a recipe in which the film stack is set to [oxide/silicon]. The thickness of the damaged layer and the polymer on the silicon may be calculated from the electrical signal according to the recipe in which the film stack is set to [oxide/damaged layer/silicon] or [oxide/polymer/damaged layer/silicon].

In further embodiments of the present invention, the methods include obtaining a difference value (ΔR) between a maximum reflectivity ($R^{max}$) and a minimum reflectivity ($R^{min}$) from the electrical signal, and comparing the difference value (ΔR) with a predetermined reference difference value to determine whether the target of measurement is over-etched. The reference difference value may be set to 0.01. An electrical output signal corresponding to light reflected from the wafer may be normalized based on a particular output signal from the bare silicon which may be set to "1" so that the electrical output signal can be used as a reference value.

BRIEF DESCRIPTION OF THE DRAWINGS

The above objectives and advantages of the present invention will become more apparent by describing in detail preferred embodiments thereof with reference to the attached drawings in which.

DETAILED DESCRIPTION OF THE PRESENT INVENTION

Figure 1:
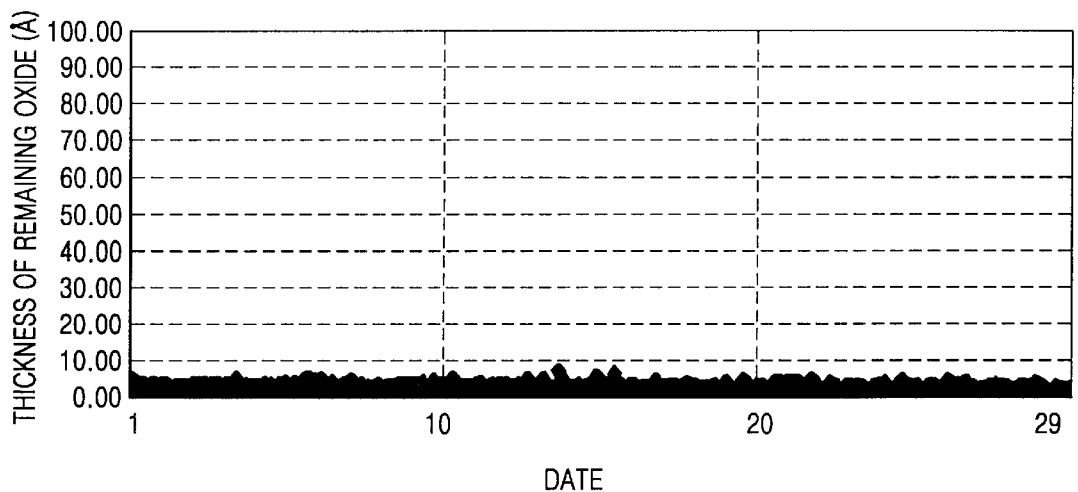
FIG. 1 is a graph showing the results of measuring the thickness of remaining oxide (Tox) using a conventional optical measuring apparatus with respect to wafers which are obtained after dry etching active silicon nitride (SiN) during manufacture of 64-M dynamic random access memory (DRAM) devices, wherein one wafer is sampled on each day in the process of accumulating measurement data.
Figure 2:
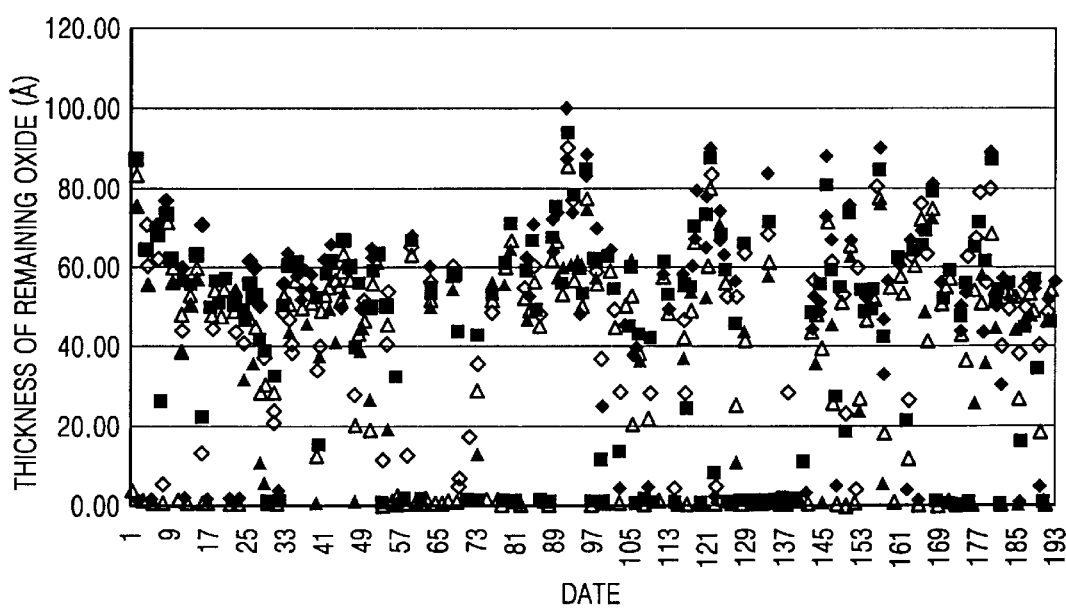
FIG. 2 is a graph showing the results of measuring the thickness of remaining oxide with respect to wafers which are obtained after over-etching the oxide for forming a DC during manufacture of 64-M DRAM devices, wherein five wafers are sampled on each day in the process of accumulating measurement data.

The present invention now will be described more fully hereinafter with reference to the accompanying drawings, in which preferred embodiments of the invention are shown. This invention may, however, be embodied in many different forms and should not be construed as limited to the embodiments set forth herein; rather, these embodiments are provided so that this disclosure will be thorough and complete, and will fully convey the scope of the invention to those skilled in the art.

As will be appreciated by one of skill in the art, the present invention may be embodied as a method, data processing system, or computer program product. Accordingly, the present invention may take the form of an entirely hardware embodiment, an entirely software embodiment or an embodiment combining software and hardware aspects. Furthermore, the present invention may take the form of a computer program product on a computer-usable storage medium having computer-usable program code means embodied in the medium. Any suitable computer readable medium may be utilized including hard disks, CD-ROMs, optical storage devices, a transmission media such as those supporting the Internet or an intranet, or magnetic storage devices.

Computer program code for carrying out operations of the present invention may be written in an object oriented programming language such as Java®), Smalltalk or C++. However, the computer program code for carrying out operations of the present invention may also be written in conventional procedural programming languages, such as the "C" programming language. The program code may execute entirely on the user's computer, partly on the user's computer, as a stand-alone software package, partly on the user's computer and partly on a remote computer or entirely on the remote computer. In the latter scenario, the remote computer may be connected to the user's computer through a local area network (LAN) or a wide area network (WAN), or the connection may be made to an external computer (for example, through the Internet using an Internet Service Provider).

The present invention is described below with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions specified in the flowchart and/or block diagram block or blocks.

Generally, while an over-etching process using plasma is being performed, atoms or ions having large energy collide with the surface of the film of a wafer causing various types of etching damage. Etching damage is usually divided into three types. In a first type, polymers which are the byproducts of reaction during plasma etching remain on the surface of a silicon substrate. In a second type, the performance of a device circuit is reduced by diffusion of impurities produced within a plasma chamber, in which etching is performed, over a dielectric film or an active device region. A third type is bonding damage in a contact region, which is caused by ions having high energy and light flux within a plasma chamber in which an etching process is performed. The forming of a direct contact (DC) and the forming of a metal contact (MC) involve under a plasma etching process which can cause damage on a silicon substrate.

Accordingly, it may be desirable to measure the degree of damage on a silicon substrate to more accurately/reliably measure the thickness of remaining oxide after an over-etching process. However, in conventional measuring equipment, a recipe for measuring remaining oxide for monitoring an over-etching process typically has a simple film stack of [oxide/silicon]. In various embodiments, the present invention may use a film stack set as [polymer/oxide/damaged layer/silicon] for the case of over-etching.

Figure 3:
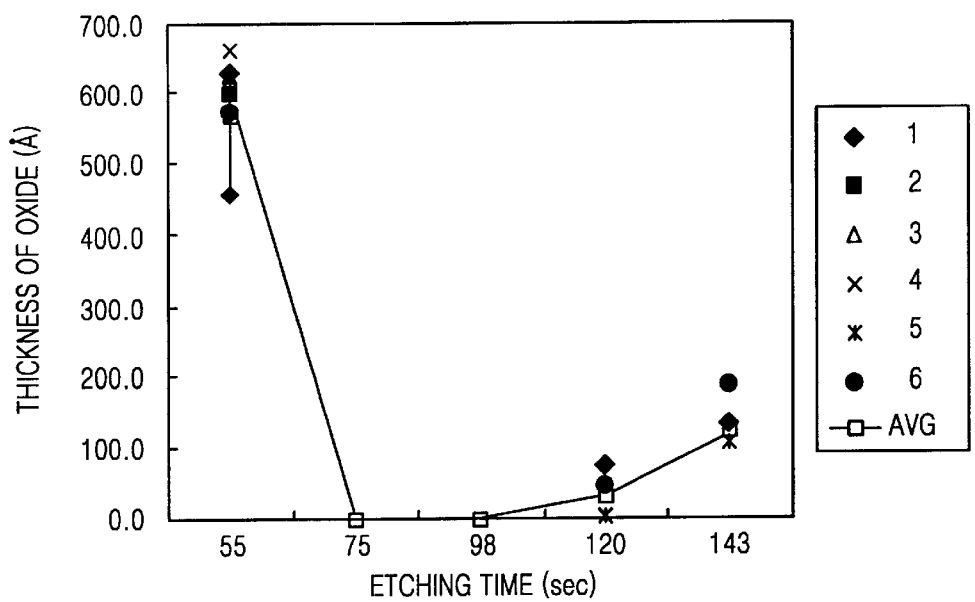
FIG. 3 is a graph showing the results of measuring the thickness of remaining oxide according to a conventional over-etching measuring method using beam profile reflectometry (BPR) based on etching time with respect to five wafers.

To illustrate the problems of a conventional over-etching measuring method, a test was performed under various measuring conditions. FIG. 3 is a graph showing the results of measuring the thickness of remaining oxide according to a conventional over-etching measuring method using beam profile reflectometry (BPR) based on etching time with respect to six wafers. Here, the film stack of a measuring recipe was set as [oxide/silicon] as in a conventional method. Over-etching time was adjusted to 55, 75, 98, 120 and 143 seconds with respect to six samples 1 through 6, and remaining oxide obtained from each sample by etching time was measured.

When the over-etching time was 55 seconds, the average thickness of remaining oxide in every sample was 600 Å, so it can be inferred that the over-etching was not successfully performed. When the over-etching time was 75 and 98 seconds, the average thickness of remaining oxide in every sample was 0 Å, so it can be inferred that the over-etching was successfully performed. However, when the over-etching time was 120 and 143 seconds, the thickness of remaining oxide, as measured, in contrast to the actual oxide thickness increased. Accordingly, it can be inferred that success or failure in over-etching may not reliably be determined by such a conventional measuring method. Results similar to those of this test were obtained from other tests using one or more of beam profile reflectometry (BPR), spectrometry and beam profile ellipsometry (BPE).

As described above, the present invention may determine the success or failure of over-etching based on change in an optical impedance. The present inventors performed a simulation under the conditions shown in Table 1 below to inspect how an optical impedance changes after over-etching using plasma. In this simulation, a reflectivity was employed as an optical impedance. For an optical method for obtaining the optical impedance of a wafer from light reflected from a wafer, one or more of BPR, spectrometry, BPE and spectroscopic ellipsometry (SE) were selected and used. The optical impedance was obtained by irradiating a wafer and spectrum-analyzing the reflected light. The radiated light may have a single wavelength or a particular wavelength band within a range from a deep ultra violet region to an infrared region. The angle of radiated light with respect to a wafer may be arbitrarily changed. For this, a lamp or a laser unit can be employed as a light source.

TABLE 1

|  | Material | Thickness | Refractive Index (N) | Extinction Coefficient (K) |
|---|---|---|---|---|
| Layer 1 | Air |  | 1 | 0 |
| Layer 2 | Damaged SI | 0–1000 Å | 4.40 | 0.01 |
| Substrate | Silicon |  | 3.822 | 0.02 |

In this simulation, a damaged layer was considered to be amorphous silicon to represent the degree (thickness) of damage to the silicon by over-etching, the wavelength of the incident light was 632.8 nm, and the incidence angle of the light was 0 so that the light was incident on a wafer perpendicularly. Based on the results of this simulation, it was analyzed how a normalized reflecivity, which is represented as a function of the thickness of amorphous silicon by an output signal, and which is proportional to the optical impedance, changes with a change in the thickness of amorphous silicon, to learn about the influence of the thickness of a damaged layer on an optical impedance.

Figure 4:
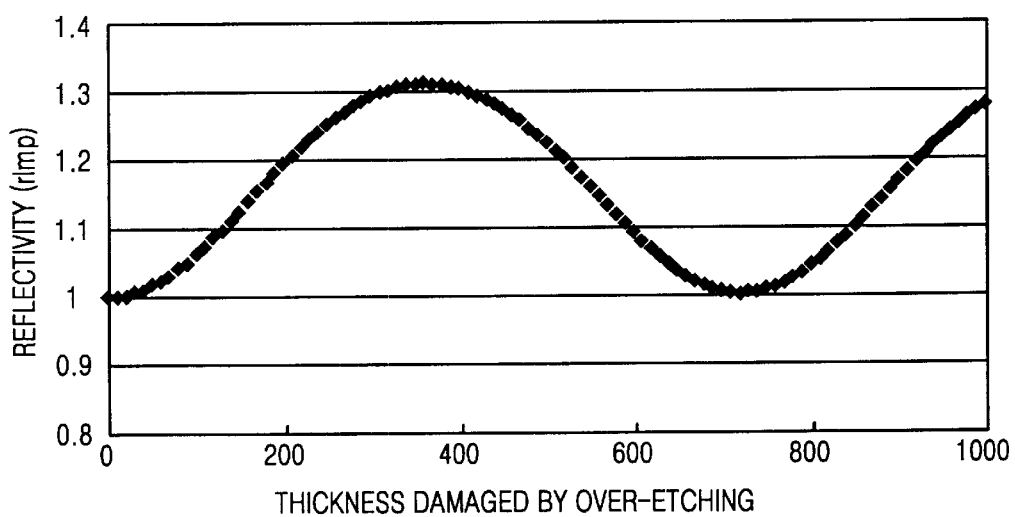
FIG. 4 is a graph showing the results of a simulation with respect to a wafer which has undergone an over-etching process, in which change in reflectivity normalized into an optical impedance by etching time is shown.

FIG. 4 is a graph showing the results of the above simulation, wherein change in a reflectivity is normalized into an optical impedance an plotted versus etching time. Referring to FIG. 4, as the degree of over-etching increases, that is, as the thickness of a damaged layer increases, an optical impedance rlmp depending on a reflectivity is 1 or larger and varies sinusoidally with etching time.

A spectrometry method using a wavelength in a visible region was applied to the 6 samples described in Table 2. In the samples 1 through 4, oxide was completely removed. In the sample 5, oxide silicon was deposited on bare silicon (a wafer) to a thickness of about 50 Å. In the sample 6, oxide was etched to a thickness of about 600 Å. A change in an optical impedance rlmp was measured. The results are shown in FIG. 5.

TABLE 2

| Sample No. | State | Etching time (sec) | Thickness of remaining oxide (Å) |
|---|---|---|---|
| 1 | Over-etching is completed. | 75 | 0 |
| 2 | Over-etching is completed. | 98 | 0 |
| 3 | Over-etching is completed. | 120 | 0 |
| 4 | Over-etching is completed. | 143 | 0 |
| 5 | Oxide remains. | 0 | 50 |
| 6 | Oxide remains. | 55 | 600 |

Figure 5:
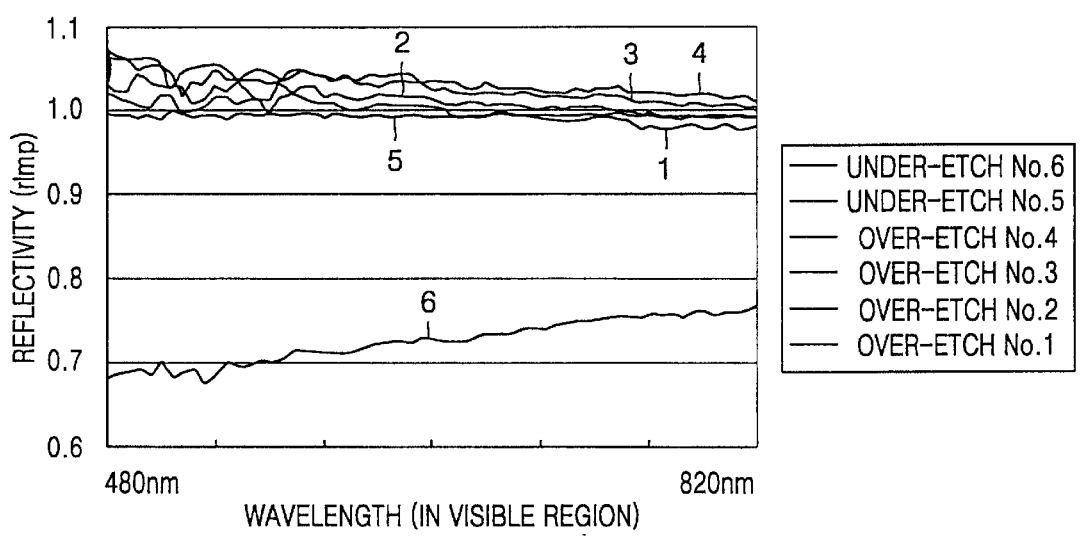
FIG. 5 is a graph showing changes in optical impedances obtained by applying a spectrometry method using a wavelength in the visible region to six samples.

In FIG. 5, the x-axis indicates a wavelength, and the y-axis indicates a normalized optical impedance rlmp. As shown in FIG. 5, the sample 6, in which the thickness of remaining oxide is 600 Å, has an optical impedance of about 0.7, which is lower than 1. The sample 5, in which the thickness of remaining oxide is 50 Å, has an optical impedance of a little lower than 1 throughout the wavelength band. Each of the samples 1 through 4 in an over-etched state has an optical impedance exceeding 1 in a wavelength band of about 600 nm and lower.

From these results, it can be inferred that the success or failure of over-etching can be determined by measuring an optical impedance in a particular wavelength band of, for example, 600 nm and lower. In other words, change in damage on silicon caused by an over-etching process on a wafer results in change in an optical impedance. In particular, when a damaged silicon layer is produced, that is, when over-etching is effected, an optical impedance has a value larger than 1.

Figure 6:
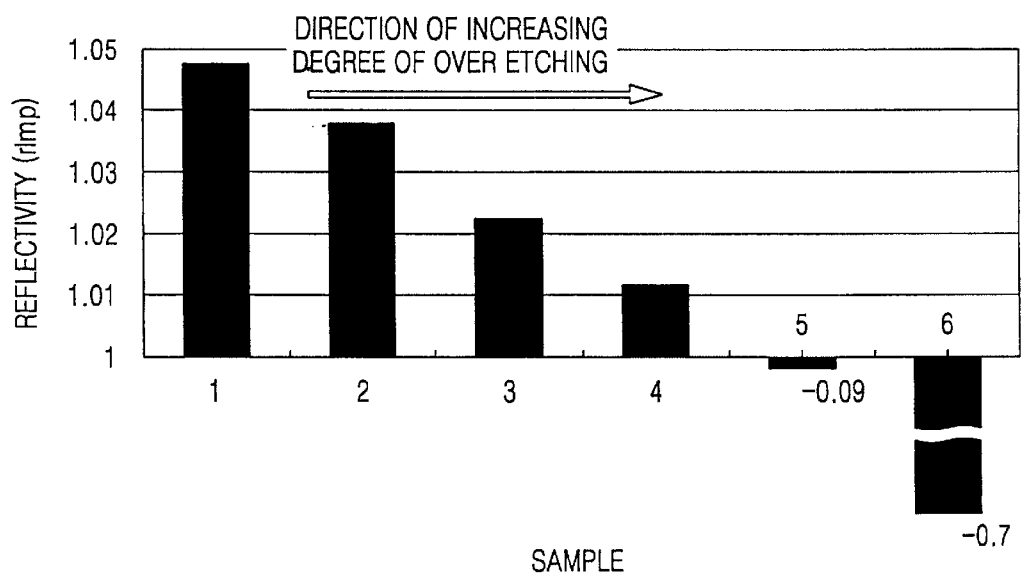
FIG. 6 is a bar graph showing values obtained by integrating an output signal of reflected light generated under the condition that light of a wavelength band of 500–530 nm is perpendicularly incident on each sample wafer which has undergone over-etching.

FIG. 6 is a bar graph showing values obtained by integrating an output signal of reflected light generated under the condition that light of a wavelength band of 500–530 nm is perpendicularly incident on each sample wafer which has undergone over-etching. The samples that were over-etched for 75, 98, 120 and 143 seconds, respectively, have optical impedances larger than 1, so it can be understood that over-etching has been completed. Since the samples 5 and 6 have optical impedances smaller than 1, it can be inferred that over-etching has not been completed. Such a determination may be applied to an actual process, for example, by a program which obtains an integrated value from an electrical signal of reflected light.

In the above case, completion or incompletion of over-etching may be determined based on an integral of values obtained from a wavelength of a predetermined band. Alternatively, completion or incompletion of over-etching may be determined based on an electrical signal of a particular single wavelength.

Figure 7:
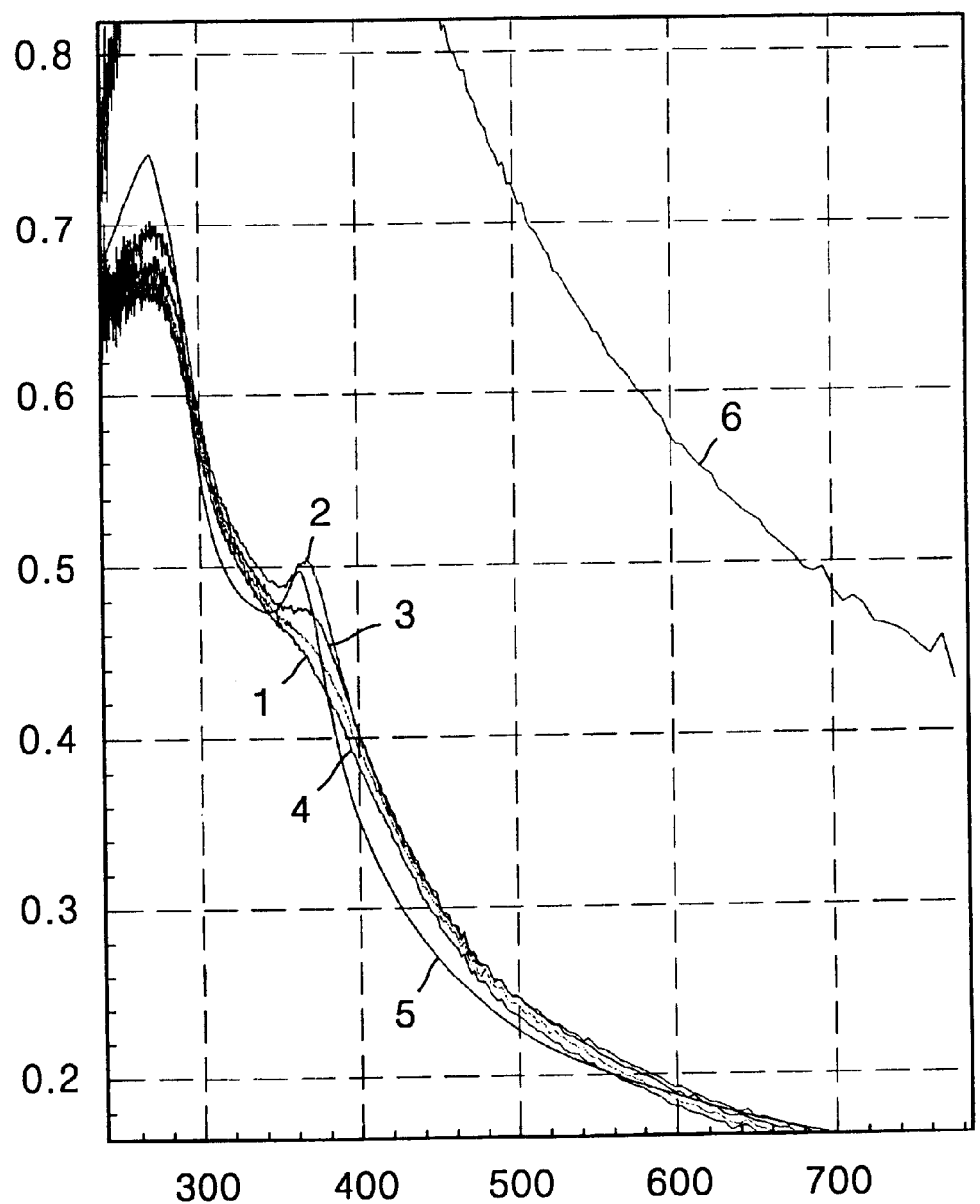
FIG. 7 is a curve showing change in a ratio Rs/Rp (TanΨ) of the reflectivity Rs of an s-polarized component to the reflectivity Rp of a p-polarized component of reflected light under the condition that light is obliquely incident on a wafer sample and bare silicon.

FIG. 7 is a curve showing change in a ratio Rs/Rp (TanΨ) of the reflectivity Rs of an s-polarized component to the reflectivity Rp of a p-polarized component of reflected light under the condition that light is obliquely incident on the samples 1, 2, 3, 4 and 6 and bare silicon 5. Referring to FIG. 7, a signal from the sample 6 having oxide with a thickness of 600 Å is larger than a signal from the bare silicon throughout the band. Signals from the other samples are smaller than a signal from the bare silicon in a wavelength band of 220–280 nm and larger than 700 nm. Here, the samples having smaller values than the value of a signal from the bare silicon 5 may be determined to be completely over-etched. Accordingly, when the ratio of the reflectivity tRs of a s-polarized component to the reflectivity tRp of a p-polarized component, light which is reflected from a wafer subject to measurement is employed as an optical impedance, the normalized optical impedance tlmp of a wafer subject to measurement can be represented by:

$$tlmp=(Rs/Rp)/(tRs/tRp) \quad (1)$$

According to Equation (1), the optical impedance of a wafer on which over-etching is completed is larger than 1, the optical impedance of a wafer in which over-etching is not completed is smaller than 1.

Figure 8:
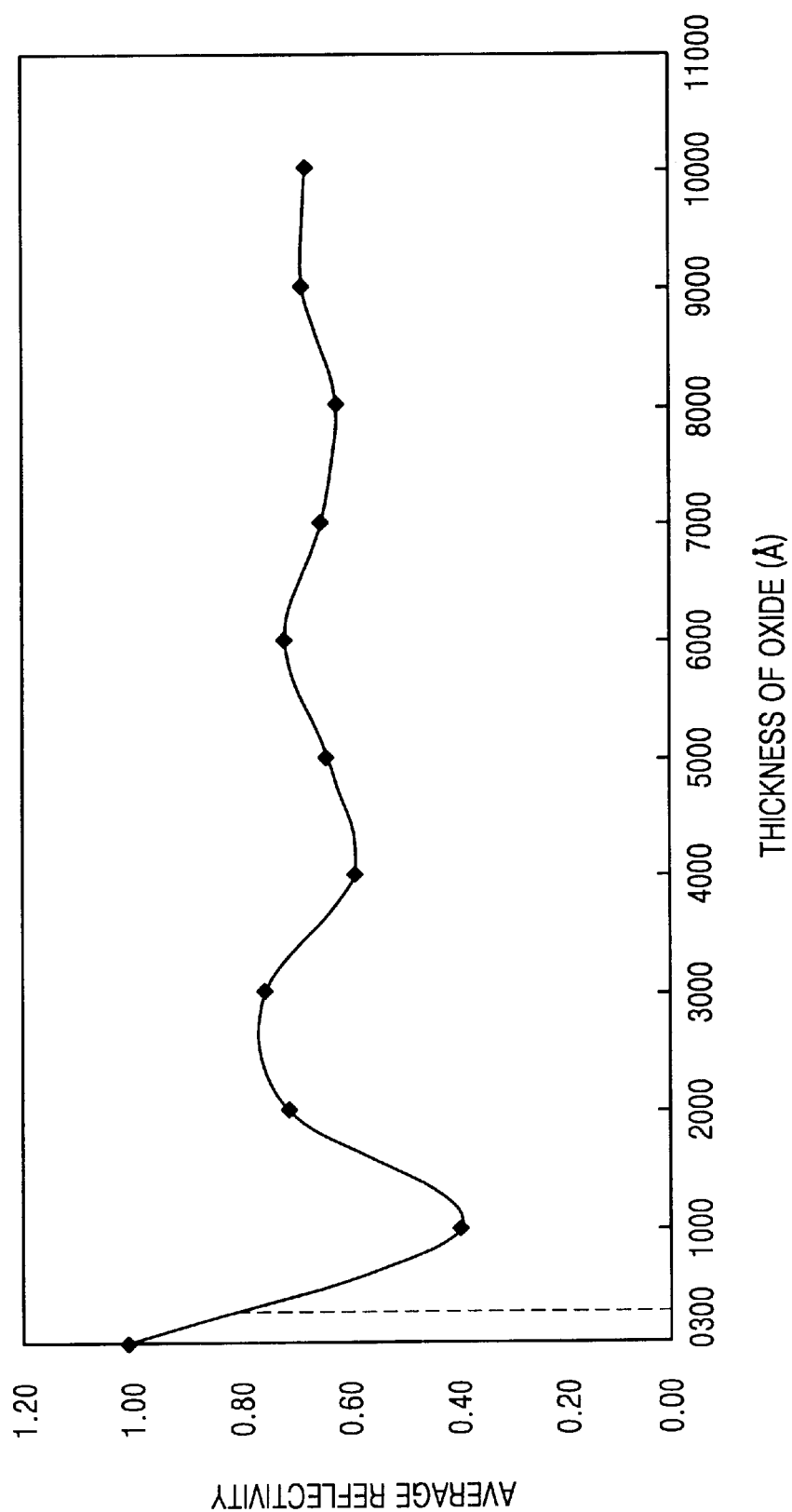
FIG. 8 shows the results of a simulation of change in the average reflectivity of light of a wavelength band of 480–820 nm depending on change in the thickness of oxide.

FIG. 8 is obtained from a simulation and shows change in an average reflectivity of light of wavelength band of 480–820 nm depending on change in the thickness of oxide. Referring to FIG. 8 as the thickness of oxide increases, a normalized reflectivity continuously decreases below 1 until the thickness of oxide is 1000 Å, and thereafter, is maintained between 0.5 and 0.8. In particular, when the thickness of oxide is 300 Å or thicker, the normalized reflectivity is always 0.8 or smaller. According to a test, this tendency appears when the wavelength of light is 480–820 nm. Accordingly, when the reflectivity of light reflected from a wafer or a normalized reflectivity with respect to a reference value of bare silicon or a normalized reference value 1 in a band of 480–820 nm, particularly, the integrated value of reflectivities in the band of 450–820 nm, is 80% or smaller, this indicates an under-etched state in which over-etching has not been completed. Here, the reference ratio may be set to 80%. It was also confirmed that the reference ratio can be set to 92% through testing.

Accordingly, an under-etched state may be determined based on an optical impedance in a band of 450–800 nm before determining an over-etched state based on optical impedances rlmp and tlmp depending on a reflectivity. In other words, it is possible to determine over-etching based on a predetermined optical impedance after performing determination on under-etching. Here, it was confirmed that the wavelength band can be extended from a range of 450–800 nm to a range of 190–826 nm through testing.

Hereinafter, various embodiments of the present invention will be described.

First Embodiment

1. An optical impedance of light reflected from bare silicon at each wavelength is normalized into a reference value, for example, 1.

2. Light having a wavelength band of 190–826 nm is radiated at a target of measurement, i.e., a wafer that has undergone an over-etching process.

3. An electrical signal normalized from light of the above band among the light reflected from the wafer is integrated.

4. It is determined whether the integrated value is larger than 92% with respect to an integrated reference value.

5. When it is determined that the integrated value does not exceed 92% with respect to the reference value, it is determined that the wafer is not completely over-etched, and the thickness of remaining oxide is measured according to an incomplete over-etching recipe.

In this first embodiment, either of the reference value and the integrated value can be replaced with the average value of an electrical signal that is not normalized.

According to the above embodiment, a wafer that is under-etched can be sorted out. When the integrated value does not exceed 92%, this embodiment may be followed by a conventional method or a method according to a second embodiment of the present invention described below.

Second Embodiment

1. An optical impedance of light reflected from bare silicon is obtained by wavelength.

2. Light of a predetermined wavelength band is radiated at a target of measurement, i.e., a wafer that has undergone an over-etching process.

3. An electrical signal is obtained from light reflected from the wafer.

4. An optical impedance normalized from an electrical signal of a predetermined wavelength band is calculated from the electrical signal obtained from the light reflected from the wafer.

5. The calculated value is compared with the reference value to determine whether or not over-etching is completed.

6. When over-etching is completed, the thickness of a damaged layer formed on the wafer is measured according to a predetermined over-etch recipe.

7. When over-etching is not completed, the thickness of remaining oxide is measured according to a predetermined under-etch recipe.

The film stack of the over-etch recipe may be set to a form of, for example, [damaged layer/silicon] or [polymer/damaged layer/silicon]. This recipe is predetermined based on a film structure appearing when over-etching is actually completed under the given over-etching conditions.

In addition, the film stack of the under-etch recipe may be set to a form of, for example, [oxide/silicon] or [polymer/oxide/silicon]. This recipe is predetermined based on a film structure appearing when over-etching is not actually completed under the given over-etching conditions.

Figure 9:
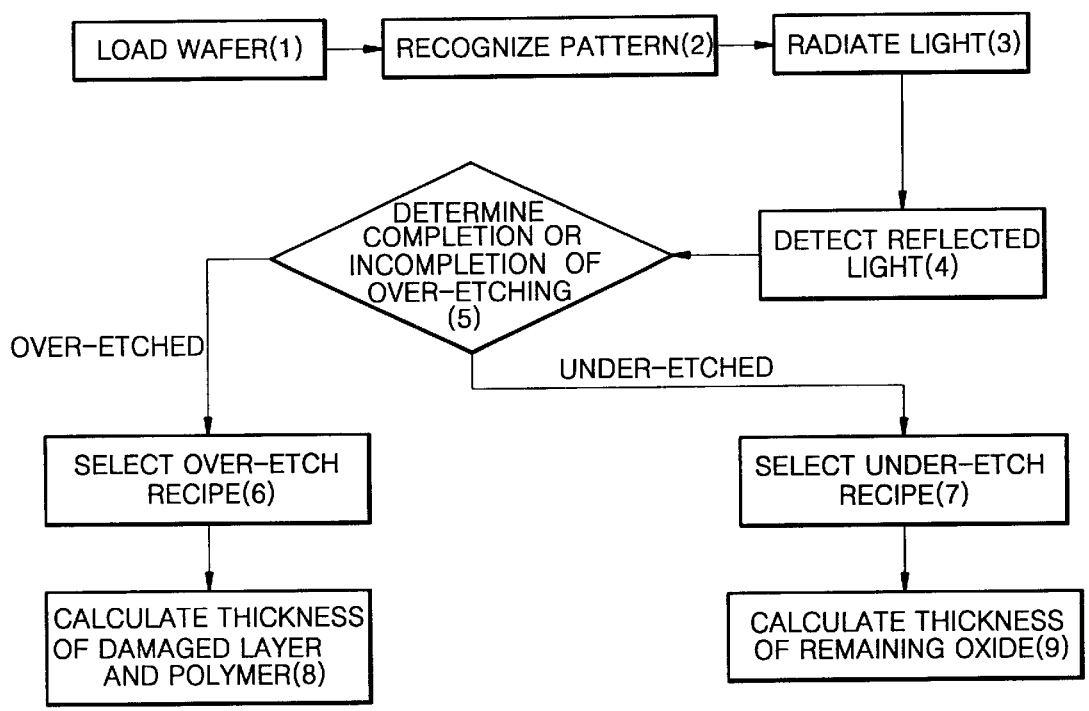
FIG. 9 is a flowchart illustrating operations according to embodiments of the present invention.

FIG. 9 is a flowchart of the second embodiment of the present invention described above.

First step: A wafer that has undergone an over-etching process is loaded (1).

Second step: The pattern of the loaded wafer is recognized (2).

Third step: The pattern i s irradiated with light (3).

Fourth step: Light reflected from the pattern is detected as an electrical signal (4).

Fifth step: The value of an optical impedance is obtained from the electrical signal and is compared with a predetermined reference value to determine completion or incompletion of the over-etching (5).

Sixth step: When the over-etching process is completed, an over-etch recipe is s elected (6).

Seventh step: When the over-etching process is not completed, an under-etch recipe is selected (7).

Eighth step: When the over-etch recipe is selected, the thickness of a damaged layer and the other material layers is calculated using the over-etch recipe (8).

Ninth step: When the under-etch recipe is selected, the thickness of remaining oxide is calculated using the under-etch recipe (9).

In this embodiment of the present invention, whether a damaged layer is formed can be determined based on change in an optical impedance, for example, change in reflectivity or change in a ratio between the reflectivities of different polarized components of light, or a combination of change in reflectivity and a ratio between the reflectivities of polarized light, thereby exactly determining completion or incompletion of over-etching and exactly measuring the thickness of, for example, a damaged layer.

A third embodiment in which the first and second embodiments are combined is described below.

Third Embodiment

1. An optical impedance of light reflected from bare silicon is obtained by wavelength.

2. Light having a first wavelength band of 190–826 nm is radiated at a target of measurement, i.e., a wafer that has undergone an over-etching process.

3. An electrical signal is obtained from light reflected from the wafer.

4. A signal corresponding to the first wavelength band among the electrical signal is normalized and integrated.

5. It is determined whether the integrated value is larger than 92% with respect to an integrated reference value.

6. When it is determined that the integrated value does not exceed 92% with respect to the reference value, it is determined that the wafer is not completely over-etched, and the thickness of remaining oxide is measured according to an incomplete over-etching recipe.

7. An optical impedance normalized from an electrical signal of a predetermined wavelength band is calculated from the electrical signal obtained from the light reflected from the wafer.

8. The calculated value is compared with the reference value to determine whether or not over-etching is completed.

9. When over-etching is completed, the thickness of a damaged layer formed on the wafer is measured according to a predetermined over-etch recipe.

10. When over-etching is not completed, the thickness of remaining oxide is measured according to a predetermined under-etch recipe.

In the first embodiment, a wafer in an under-etched state is sorted out by a single determination step. In the second embodiment, it is determined whether or not over-etching is completed.

According to the present invention, two determination steps may be employed as in the above third embodiment, or more than two determination steps may be employed as in succeeding embodiments. Such a multi-step determination method can be applied to a wafer that is determined to be incompletely over-etched. Such methods may facilitate determining of completion or incompletion of over-etching with respect to a wafer that may have conventionally been determined to be incompletely over-etched when, in fact, it was completely over-etched. Such additional determination may also be based on change in an optical impedance.

Figure 10:
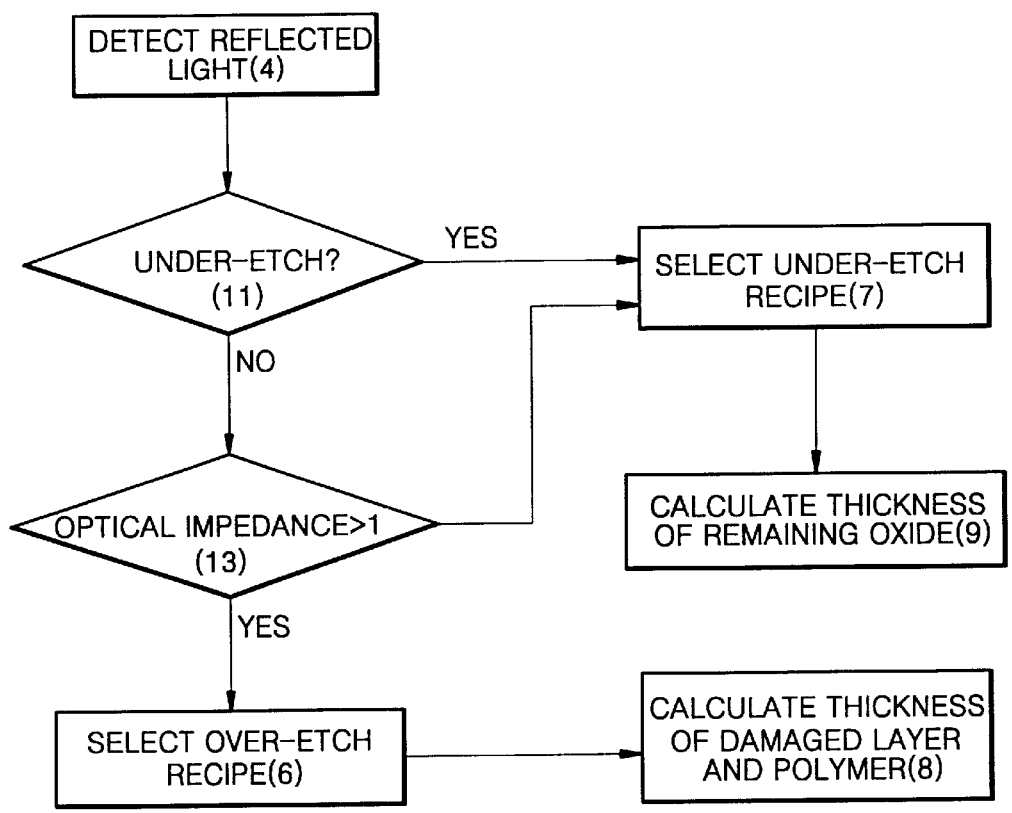
FIG. 10 is a flowchart illustrating operations according to further embodiments of the present invention.

FIG. 10 is a flowchart of the above third embodiment.

First step: Light reflected from the pattern is detected as an electrical signal (4).

Second step: It is determined that the integrated value of the electrical signal of light of a predetermined wavelength band, for example, 190–826 nm, exceeds 80% of a reference value, and under-etching is determined when the integrated value does not exceed 80% (11).

Third step: When under-etching is determined in the second step, an under-etch recipe is selected (7).

Fourth step: When the under-etch recipe is selected, the thickness of oxide is measured using the under-etch recipe (9).

Fifth step: The value of a normalized optical impedance of a particular wavelength band is obtained from the electrical signal and is compared with a predetermined reference value to determined completion or incompletion of the over-etching (13).

Sixth step: When the over-etching process is completed, an over-etch recipe is selected (6).

Seventh step: When the over-etching process is not completed, an under-etch recipe is selected (7).

Eighth step: When the over-etch recipe is selected, the thickness of a damaged layer and the other material layers is calculated using the over-etch recipe (8).

Ninth step: When the under-etch recipe is selected, the thickness of remaining oxide is calculated using the under-etch recipe (9).

Fourth Embodiment

Figure 11:
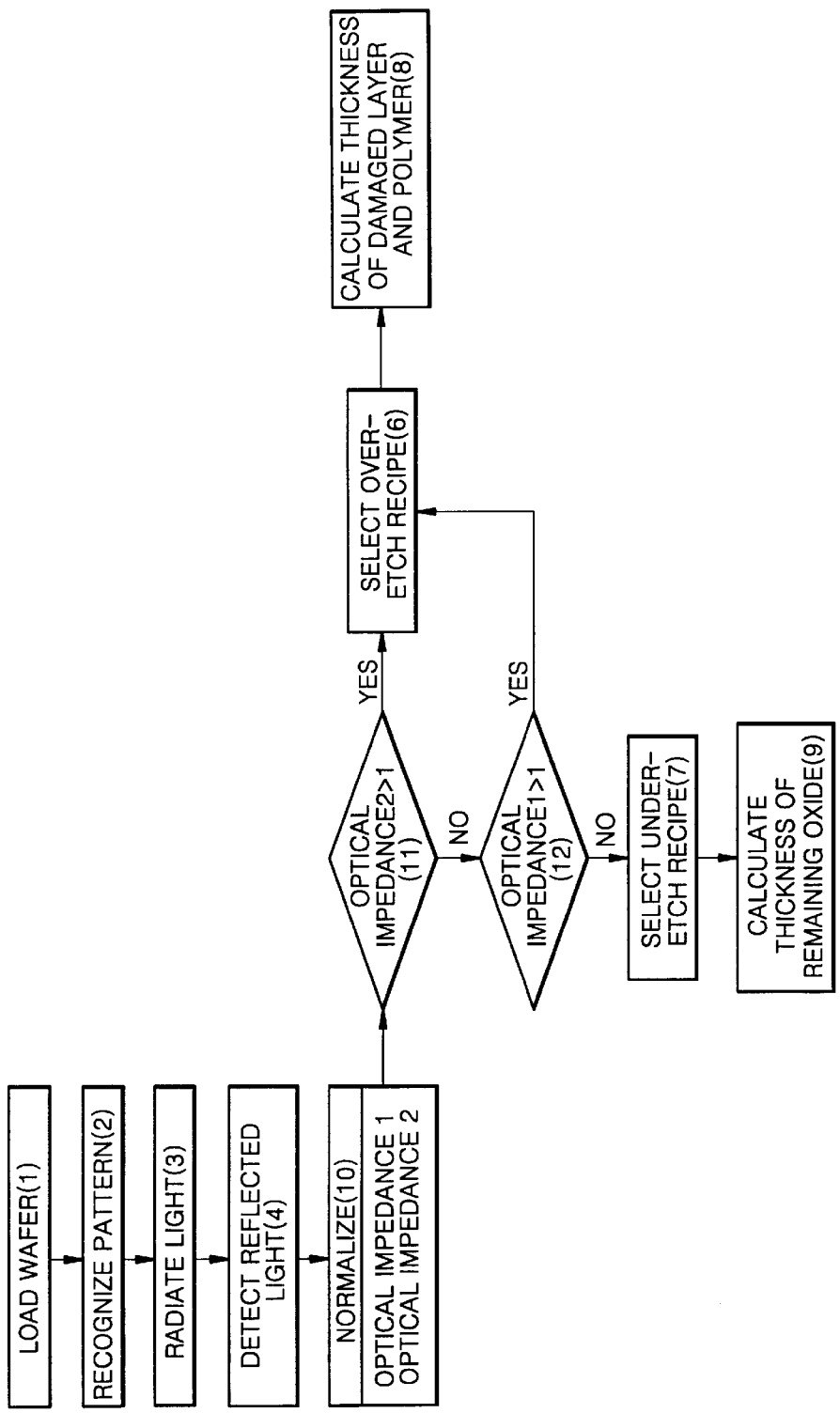
FIG. 11 is a flowchart illustrating operations according to yet further embodiments of the present invention.

With reference to FIG. 11, a fourth embodiment will be described.

First step: A wafer that has undergone an over-etching process is loaded (1).

Second step: The pattern on the loaded wafer is recognized (2).

Third step: The pattern is irradiated with light (3).

Fourth step: Light reflected from the pattern is detected as an electrical signal, and normalized optical impedances 1 and 2 are obtained from the detected light (4). An impedance rlmp depending on change in a reflectivity may be used as the optical impedance 1, and an impedance tlmp depending on change in a polarization ratio may be used as the optical impedance 2.

Fifth step: The optical impedance 1 is compared with a predetermined reference value 1 to determine completion or incompletion of the over-etching (11).

Sixth step: When the over-etching process is completed, an over-etch recipe is selected (6).

Seventh step: When it is determined that the over-etching process is not completed in the fifth step, the optical impedance 2 is compared with a predetermined reference value 2 to determined completion or incompletion of the over-etching (12).

Eighth step: When it is determined that the over-etching process is not completed in the seventh step, an under-etch recipe is selected (7).

Ninth step: When the over-etch recipe is selected, the thickness of a damaged layer and the other material layers is calculated using the over-etch recipe (8).

Tenth step: When the under-etch recipe is selected, the thickness of remaining oxide is calculated using the under-etch recipe (9).

This embodiment of the present invention determines whether over-etching is completed using the optical impedance 2 with respect to a wafer that is determined to be incompletely over-etched in the first phase of determination in the fifth step using the optical impedance 1. This may on occasion sort out a wafer in which over-etching is completed.

Meanwhile, the first embodiment may be introduced between the third step and the fourth step of the fourth embodiment. In this case, a wafer in an under-etched state is primarily sorted out, and then the two determination steps using the optical impedances rlmp and tlmp are performed, thereby further discriminating a completely over-etched wafer from an under-etched wafer in the embodiments described above. In particular, a desired measurement can be performed on wafers in different states.

The embodiments described above can be carried out according to the present invention. Determination of the state of a wafer can be made based on conditions such as optical impedances as described above, without limitation of the number of times.

Fifth Embodiment

This embodiment is provided for further determining the etch state of a sample. In particular, the result of a test showed that there are some cases where a sample is actually under-etched even if it is determined to be over-etched in the above embodiments. Therefore, in this embodiment, a step for further determining the etch state of a sample will be described.

A minimum reflectivity $R^{min}$ is calculated from the reflectance curve of a spectrometer, which may be obtained from an image array of a predetermined number of pixels, for example, 256 pixels, in a wavelength band of 720–826 nm. A maximum reflectivity $R^{max}$ is obtained in a wavelength band of 550–720 nm.

A difference value $\Delta R$ between the maximum reflectivity and the minimum reflectivity can be represented by Equation (2).

$$\Delta R = R^{max} - R^{min} \quad (2)$$

1) Here, when $\Delta R<0.01$, it is determined that a given sample is under-etched. When it is determined that a sample is under-etched under this condition, measurement is performed using an under-etch recipe without the need for further attempts at a more exact determination. Here, a comparative reference value 0.01 is obtained through trial and error testing and is useful to determine the etch state of a sample.

2) When $\Delta R>0.01$, over-etching or under-etching of a sample may be determined based on the following conditions depending on an average reflectivity $R^{AVG}$ obtained from the spectrometer reflectance curve in a wavelength band of 550–826 nm.

When $\Delta R>0.01$ and $R^{AVG} \geq 0.9$, it is determined that a sample is over-etched. Alternatively, when $\Delta R>0.01$ and $R^{AVG}<0.9$, it is determined that a sample is under-etched, and measurement is performed using an under-etch recipe without more determination.

The step described above may be performed between the steps 3 and 4, between the steps 4 and 5 or after the step 5 in the first embodiment.

In the case where this step is performed between the steps 3 and 4, when $\Delta R$ is smaller than 0.01, it is finally determined that a sample is under-etched, and the thickness of remaining oxide may be immediately measured using the under-etch recipe. When $\Delta R$ is equal to or larger than 0.01, the steps 4 and 5 are sequentially performed, and then it may be finally determined whether a sample is over-etched.

In the case where this step is performed between the steps 4 and 5 or after the step 5, when $\Delta R$ is smaller than 0.01 with respect to a sample that is determined to be over-etched in the step of determining completion or incompletion of over-etching based on the reference ratio of 92%, it is finally determined that the sample is under-etched. When $\Delta R$ is equal to or larger than 0.01, it is finally determined that the sample is over-etched.

The above fifth embodiment can be applied to the second through fourth embodiments. A first step of determining an over-etch state based on the reference ratio of 92% or the change in an impedance as described in the first through fourth embodiments, and a second step of determining an over-etch state based on $\Delta R$ as described in the fifth embodiment may be applied to these second through fourth embodiments. When it is determined that a sample is under-etched in the two determination steps, it is finally concluded that the sample is under-etched, and the thickness of oxide may be measured using the under-etch recipe. Alternatively, when it is determined that a sample is over-etched in either of the first and second determination steps, the over-etched state of the sample is determined again using the second or first determination step. Through a test, it was concluded that it is not necessary to perform determination by comparing the reference ratio 92% with the ratio of an output value to a reference value as described before with respect to a sample that is determined to be under-etched based on the conditions of the fifth embodiment. In addition, through a test, it was concluded that it is not necessary to perform determination of an over-etched state based on $\Delta R$ with respect to a sample that is determined to be under-etched in the first through fourth embodiments.

According to the present invention, completion or incompletion and the degree of over-etching may be measured. Such measurements may aid in control of process failures caused by measurement error. In addition, the present invention may be used to determine completion or incompletion of over-etching. This may improve the yield of semiconductor devices and allow the degree of over-etching on a wafer which has undergone over-etching to be monitored.

The flowcharts and block diagrams of FIGS. 9 through 11 illustrate the architecture, functionality, and operation of possible implementations of systems, methods and computer program products for measuring a semiconductor wafer according to various embodiments of the present invention. In this regard, each block in the flow charts or block diagrams may represent a module, segment, or portion of code, which comprises one or more executable instructions for implementing the specified logical function(s). It should also be noted that, in some alternative implementations, the functions noted in the blocks may occur out of the order noted in the figures. For example, two blocks shown in succession may, in fact, be executed substantially concurrently, or the blocks may sometimes be executed in the reverse order, depending upon the functionality involved.

In the drawings and specification, there have been disclosed typical preferred embodiments of the invention and, although specific terms are employed, they are used in a generic and descriptive sense only and not for purposed of limitation, the scope of the invention being set forth in the following claims.

What is claimed is:

1. A method for measuring a semiconductor wafer which has been subjected to an etching process, the method comprising the steps of:

Radiating light at the semiconductor wafer;

Measuring light within a selected wavelength band reflected from the semiconductor wafer to provide an output value;

Determining a ratio of the output value and a reference value, the reference value being based on light within the selected wavelength band reflected from a reference surface; and Determining that the semiconductor wafer is under-etched if the determined ratio does not meet a reference ratio.

2. The method of claim 1 wherein the selected wavelength band extends no lower than about 190 nanometers(nm) and no higher than about 826 nm and wherein the reference ratio is at least about 80%.

3. The method of claim 2 wherein the reference ratio is about 92% and wherein the radiating step further comprises the step of radiating light within the selected wavelength band at the semiconductor wafer, the radiated light having an incidence angle with reference to the semiconductor wafer of about 0 degrees.

4. A method for measuring a semiconductor wafer which has been subjected to an etching process, the method comprising the steps of:

radiating light at the semiconductor wafer;

measuring light within a selected wavelength band reflected from the semiconductor wafer to provide an output value;

determining a ratio of the output value and a reference value, the reference value being based on light within the selected wavelength band reflected from a reference surface; and determining that the semiconductor wafer is under-etched if the determined ratio does not meet a reference ratio; and measuring light in the selected wavelength band reflected from a bare silicon reference surface to provide the reference value.

5. The method of claim 1 wherein the step of measuring light reflected from the semiconductor wafer further comprises the step of measuring an average value of an electrical signal generated by reflected light in the selected wavelength band.

6. The method of claim 1 wherein the step of measuring light reflected from the semiconductor wafer further comprises the steps of determining a first reflectivity value based on a first portion of the selected wavelength band and a second reflectivity value based on a second portion of the selected wavelength band different from the first portion and wherein the method further comprises the steps of:

determining a difference value between the first reflectivity and the second reflectivity; and determining that the semiconductor wafer is under-etched if the difference value does not satisfy a reference difference value.

7. The method of claim 6 wherein the reference difference value is about 0.01 and wherein the step of determining that the semiconductor wafer is under-etched if the difference value does not satisfy a reference difference value comprises the step of determining that the semiconductor wafer is under-etched if the difference value is less than the reference difference value.

8. The method of claim 1 wherein the step of measuring the light reflected from the semiconductor wafer further comprises the step of integrating an electrical signal generated by reflected light in the selected wavelength band.

9. A method for measuring a semiconductor wafer which has been subjected to an etching process, the method comprising the steps of:

radiating light at the semiconductor wafer;

measuring light within a selected wavelength band reflected from the semiconductor wafer to provide an output value;

determining a ratio of the output value and a reference value, the reference value being based on light within the selected wavelength band reflected from a reference surface; and determining that the semiconductor wafer is under-etched if the determined ratio does not meet a reference ratio; and wherein the step of measuring the light reflected from the semiconductor wafer further comprises the step of measuring a polarization ratio of light reflected from the semiconductor wafer to provide the output value.

10. The method of claim 9 wherein the polarization ratio comprises a ratio of reflectivity of an s-polarized component of the reflected light and a p-polarized component of the reflected light.

11. The method of claim 9 further comprising the step of determining a thickness of remaining oxide using an under-etch recipe when it is determined that the semiconductor wafer is under-etched.

12. The method of claim 11 further comprising the step of determining a thickness of a damaged/polymer layer using an over-etch recipe when it is determined that the semiconductor wafer is over-etched.

13. The method of claim 12 wherein the over-etch recipe uses a predetermined over-etching completed film stack and wherein the under-etch recipe uses a predetermined over-etching incompleted film stack.

14. The method of claim 13 wherein the over-etching completed film stack is set to polymer/oxide/damaged layer/silicon and the over-etching incompleted film stack is set to oxide/silicon.

15. The method of claim 12 wherein the step of determining that the semiconductor wafer is under-etched is followed by the following steps if the semiconductor wafer is not determined to be under-etched:

generating a normalized optical impedance (rlmp) for a reflectivity wavelength band based on light reflected from the semiconductor wafer;

comparing the normalized optical impedance (rlmp) to a rlmp reference value; and determining that the semiconductor wafer is over-etched if the normalized optical impedance (rlmp) meets the rlmp reference value.

16. The method of claim 15 wherein the rlmp reference value is based on light reflected from a bare silicon reference surface and further comprising the step of determining that the semiconductor wafer is under-etched if the normalized optical impedance (rlmp) does not meet the rlmp reference value.

17. The method of claim 15 further comprising the following steps performed if the semiconductor wafer is not determined to be under-etched and is not determined to be over-etched:

generating a polarization ratio for a polarization wavelength band based on light reflected from the semiconductor wafer;

comparing the polarization ratio to a polarization reference value;

determining that the semiconductor wafer is over-etched if the polarization ratio meets the polarization reference value; and determining that the semiconductor wafer is under-etched if the normalized optical impedance (rlmp) does not meet the rlmp reference value and the polarization ratio does not meet the polarization value.

18. The method of claim 17 wherein the polarization wavelength band extends no lower than about 220 nm and no higher than about 280 nm and wherein the polarization ratio comprises a ratio of reflectivity of an s-polarized component of reflected light and a p-polarized component of reflected light.

19. The method of claim 17 wherein the step of determining that the semiconductor wafer is under-etched if the determined ratio does not meet a reference ratio is followed by the following steps if the semiconductor wafer is not determined to be under-etched:

determining a first reflectivity value based on a first portion of the selected wavelength band;

determining a second reflectivity value based on a second portion of the selected wavelength band different from the first portion;

determining a difference value between the first reflectivity and the second reflectivity; and determining that the semiconductor wafer is under-etched if the difference value does not satisfy a reference difference value.

20. The method of claim 12 wherein the step of determining that the semiconductor wafer is under-etched is followed by the following steps if the semiconductor wafer is not determined to be under-etched:

generating a polarization ratio for a polarization wavelength band based on light reflected from the semiconductor wafer;

comparing the polarization ratio to a polarization reference value;

determining that the semiconductor wafer is over-etched if the polarization ratio meets the polarization reference value; and determining that the semiconductor wafer is under-etched if the polarization ratio does not meet the polarization value.

21. A method of determining the etched state of a semiconductor wafer, the method comprising the steps of:

radiating light a t bare silicon and obtaining a reference value from an electrical signal generated by light within a predetermined wavelength band of the light reflected from the bare silicon;

radiating light within the predetermined wavelength band at a target of measurement, i.e., a wafer that has undergone an over-etching process;

obtaining an output value corresponding to the reference value from an electrical signal generated by light within the predetermined wavelength band of the light reflected from the wafer;

calculating the ratio of the output value to the reference value; and comparing the calculated ratio with a predetermined reference ratio to determine whether or not the wafer is under-etched.

22. The method of claim 21, wherein each of the reference value and the output value is obtained from the average value of the corresponding electrical signal.

23. The method of claim 21, wherein each of the reference value and the output value is obtained from the normalized average value of the corresponding electrical signal.

24. The method of claim 22, wherein each of the reference value and the output value is obtained from the normalized average value of the corresponding electrical signal.

25. The method of claim 21, wherein the reference ratio is set to 92%.

26. The method of claim 25, wherein the predetermined wavelength band is set to a range of 190–826 nm.

27. The method of claim 21, wherein the pre determined wavelength band is set to a range of 190–826 nm.

28. The method of claim 21, further comprising the steps of:

obtaining a difference value ($\Delta R$) between a maximum reflectivity ($R^{max}$) and a minimum reflectivity ($R^{min}$) from the electrical signal; and comparing the difference value ($\Delta R$) with a predetermined reference difference value to determine whether or not the target of measurement is over-etched.

29. The method of claim 28, wherein the reference difference value is 0.01.

30. The method of claim 25, further comprising the steps of:

obtaining a difference value ($\Delta R$) between a maximum reflectivity ($R^{max}$) and a minimum reflectivity ($R^{min}$) from the electrical signal; and comparing the difference value ($\Delta R$) with a predetermined reference difference value to determine whether or not the target of measurement is over-etched.

31. The method of claim 30, wherein the reference difference value is 0.01.

32. A method of determining the etched state of a semiconductor wafer, the method comprising the steps of:

radiating light at bare silicon and obtaining a reference value by integrating an electrical signal generated by light within a predetermined wavelength band which is reflected from the bare silicon;

radiating light within the predetermined wavelength band at a target of measurement, i.e., a wafer that has undergone an over-etching process;

obtaining an output value by integrating an electrical signal of the predetermined wavelength band of light reflected from the wafer;

calculating a ratio of the output value to the reference value; and comparing the calculated ratio with a predetermined reference ratio to determine whether or not the wafer is under-etched.

33. The method of claim 32, wherein each of the reference value and the output value is obtained from a corresponding normalized electrical output.

34. The method of claim 33, wherein the reference ratio is set to 92%.

35. The method of claim 32, wherein the reference ratio is set to 92%.

36. The method of claim 32, wherein the p redetermined wavelength band is set to a range of 190–826 nm.

37. The method of claim 32, further comprising the steps of:

obtaining a difference value ($\Delta R$) between a maximum reflectivity ($R^{max}$) and a minimum reflectivity ($R^{min}$) from the electrical signal; and comparing the difference value ($\Delta R$) with a predetermined reference difference value to determine whether or not the target of measurement is over-etched.

38. The method of claim 37, wherein the reference difference value is 0.01.

39. A method of measuring the etched state of a semiconductor wafer, the method comprising:

a first step of radiating light within a predetermined wavelength band at a wafer that has undergone a plasma over-etching process;

a second step of obtaining a predetermined output value from an electrical signal corresponding to light reflected from the wafer;

a third step of determining whether an optical impedance of the light reflected from the wafer changes based on the output value;

a fourth step of determining whether the over-etching process is successfully completed depending on the change in the optical impedance determined in the third step;

a fifth step of measuring the thickness of a wafer film according to a recipe employing a predetermined over-etching completed film stack when it is determined that the over-etching process is successfully completed; and a sixth step of measuring the thickness of a wafer film according to a recipe employing a predetermined over-etching incompleted film stack when it is determined that the over-etching process is not successfully completed.

40. The method of claim 39, wherein in the second step the output value is obtained from a normalized electrical signal, and in the third step a reference value obtained from a normalized electrical signal generated by light reflected from bare silicon with the output value to determine the change in the optical impedance.

41. The method of claim 39, wherein the electrical signal is generated by light reflected from the wafer, and corresponds to the reflectivity of the wafer.

42. The method of claim 39, wherein the electrical signal corresponds to the polarization ratio of the light reflected from the wafer.

43. The method of claim 42, wherein the polarization ratio is a ratio of the reflectivity for an s-polarized component of the reflected light to the reflectivity for a p-polarized component of the reflected light.

44. The method of claim 39, wherein the over-etching completed film stack is set to [polymer/oxide/damaged layer/silicon], and the over-etching incompleted film stack is set to [oxide/silicon].

45. The method of claim 39, further comprising the steps of:
obtaining a difference value ($\Delta R$) between a maximum reflectivity ($R^{max}$) and a minimum reflectivity ($R^{min}$) from the electrical signal; and
comparing the difference value ($\Delta R$) with a predetermined reference difference value to determine whether or not the target of measurement is over-etched.

46. The method of claim 45, wherein the reference difference value is 0.01.

47. A method of measuring the etched state of a semiconductor wafer, the method comprising:
a first step of radiating light at bare silicon and obtaining a reference value 1 from an electrical signal generated by light within a predetermined wavelength band among the light reflected from the bare silicon;
a second step of radiating light within the predetermined wavelength band at a target of measurement, i.e., a wafer that has undergone an over-etching process;
a third step of obtaining an output value 1 corresponding to the reference value 1 from an electrical signal of light within the predetermined wavelength band among the light reflected from the wafer;
a fourth step of calculating a ratio of the output value 1 to the reference value 1;
a fifth step of comparing the calculated ratio with a predetermined reference ratio to determine whether or not the wafer is under-etched;
a sixth step of measuring the thickness of remaining oxide using a predetermined under-etch recipe when it is determined that the wafer is under-etched;
a seventh step of obtaining a predetermined output value 2 from an electrical signal corresponding to light reflected from the wafer when it is determined that the wafer is not under-etched;
an eighth step of determining whether an optical impedance to the light reflected from the wafer changes based on the output value 2;
a ninth step of determining whether or not the over-etching process is successfully completed depending on the change in the optical impedance determined in the above step;
a tenth step of measuring the thickness of a wafer film according to a recipe employing a predetermined over-etching completed film stack when it is determined that the over-etching process is successfully completed; and
an eleventh step of measuring the thickness of a wafer film according to a recipe employing a predetermined over-etching incompleted film stack when it is determined that the over-etching process is not successfully completed.

48. The method of claim 47, wherein each of the reference value 1 and the output value 1 is obtained from the average value of the corresponding electrical signal.

49. The method of claim 47, wherein each of the reference value 1 and the output value 1 is obtained from the normalized average value of the corresponding electrical signal.

50. The method of claim 48, wherein each of the reference value 1 and the output value 1 is obtained from the normalized average value of the corresponding electrical signal.

51. The method of claim 47, wherein the reference ratio is set to 92%.

52. The method of claim 51, wherein the predetermined wavelength band is set to a range of 190–826 nm.

53. The method of claim 47, wherein the predetermined wavelength band is set to a range of 190–826 nm.

54. The method of claims 47, wherein the over-etching completed film stack is set to [polymer/oxide/damaged layer/silicon], and the over-etching incompleted film stack is set to [oxide/silicon].

55. The method of claim 51, wherein the over-etching completed film stack is set to [polymer/oxide/damaged layer/silicon], and the over-etching incompleted film stack is set to [oxide/silicon].

56. The method of claims 47, further comprising the steps of:
obtaining a difference value ($\Delta R$) between a maximum reflectivity ($R^{max}$) and a minimum reflectivity ($R^{min}$) from the electrical signal; and
comparing the difference value ($\Delta R$) with a predetermined reference difference value to determine whether or not the target of measurement is over-etched.

57. The method of claim 56, wherein the reference difference value is 0.01.

58. A method of measuring the etched state of a semiconductor wafer, the method comprising:
a first step of radiating light within a predetermined wavelength band at a wafer that has undergone a plasma over-etching process;
a second step of obtaining predetermined optical impedances 1 and 2 from an electrical signal corresponding to light reflected from the wafer;
a third step of comparing the optical impedance 1 with a predetermined reference impedance 1 to determine whether or not the wafer is completely over-etched;
a fourth step of measuring the thickness of a wafer film according to a recipe employing a predetermined over-etching completed film stack when it is determined that the over-etching process is successfully completed in the third step;
a fifth step of comparing the optical impedance 1 with a predetermined reference impedance 1 to determine whether or not the wafer is completely over-etched when it is determined that the over-etching process is not completed in the third step;
a sixth step of measuring the thickness of a wafer film according to a recipe employing a predetermined over-etching completed film stack when it is determined that the over-etching process is successfully completed in the fifth step; and
a seventh step of measuring the thickness of a wafer film according to a recipe employing a predetermined over-etching incompleted film stack when it is determined that the over-etching process is not successfully completed.

59. The method of claim 58, wherein at least one of the optical impedances 1 and 2 is obtained from a normalized electrical signal, and at least one of the reference impedances 1 and 2 is obtained from a normalized electrical signal generated by light reflected from bare silicon.

60. The method of claim 58, wherein either of the reference impedances 1 and 2 is obtained from the reflectivity of bare silicon, and either of the optical impedances 1 and 2 is obtained from the reflectivity of the wafer.

61. The method of claim 58, wherein either of the reference impedances 2 and 1 is obtained from the polarization ratio of light reflected from bare silicon, the polarization ratio being a ratio of the reflectivity for an s-polarized component of the reflected light to the reflectivity for a p-polarized component of the reflected light, and wherein either of the optical impedances 2 and 1 is obtained from the polarization ratio of light reflected from wafer, the polarization ratio being a ratio of the reflectivity for an s-polarized component of the reflected light to the reflectivity for a p-polarized component of the reflected light.

62. The method of claim 58, wherein either of the reference impedances 1 and 2 is obtained from the reflectivity of bare silicon, and either of the optical impedances 1 and 2 is obtained from the reflectivity of the wafer, wherein either of the reference impedances 2 and 1 is obtained from the polarization ratio of light reflected from bare silicon, the polarization ratio being a ratio of the reflectivity for an s-polarized component of the reflected light to the reflectivity for a p-polarized component of the reflected light, and wherein either of the optical impedances 2 and 1 is obtained from the polarization ratio of light reflected from wafer, the polarization ratio being a ratio of the reflectivity for an s-polarized component of the reflected light to the reflectivity for a p-polarized component of the reflected light.

63. The method of claims 58, wherein the over-etching completed film stack is set to [polymer/oxide/damaged layer/silicon], and the over-etching incompleted film stack is set to [oxide/silicon].

64. The method of claim 62, wherein the over-etching completed film stack is set to [polymer/oxide/damaged layer/silicon], and the over-etching incompleted film stack is set to [oxide/silicon].

65. The method of claim 58, further comprising the steps of:

obtaining a difference value ($\Delta R$) between a maximum reflectivity ($R^{max}$) and a minimum reflectivity ($R^{min}$) from the electrical signal; and comparing the difference value ($\Delta R$) with a predetermined reference difference value to determine whether or not the target of measurement is over-etched.

66. The method of claim 65, wherein the reference difference value is 0.01.

67. A method for measuring a semiconductor wafer which has been subjected to an etching process, the method comprising the steps of:

Radiating light at the semiconductor wafer;

Measuring light within a selected wavelength band reflected from the semiconductor wafer to provide an output value;

Determining a ratio of the output value and a reference value, the reference value being based on light within the selected wavelength band reflected from a reference surface different from the semiconductor wafer; and Determining that the semiconductor wafer is under-etched if the determined ratio does not meet a reference ratio.

* * * * *